United States Patent [19]

Dugué

[11] Patent Number: 5,028,381
[45] Date of Patent: Jul. 2, 1991

[54] DEVICE FOR THE ULTRASONIC NON-DESTRUCTIVE TESTING OF A CIRCULAR WELD INSIDE A STEAM GENERATOR TUBE

[75] Inventor: Christian Dugué, Le Grand, France

[73] Assignee: Framatome, Courbevoie, France

[21] Appl. No.: 390,933

[22] Filed: Aug. 7, 1989

[30] Foreign Application Priority Data

Aug. 5, 1988 [FR] France .................. 88 10625

[51] Int. Cl.$^5$ ............................................. G21C 17/00
[52] U.S. Cl. ................................... 376/252; 376/245; 376/250; 376/249
[58] Field of Search ............... 376/245, 250, 249, 252; 73/633, 632, 623

[56] References Cited

U.S. PATENT DOCUMENTS

| 4,037,465 | 7/1977 | Cook | 73/67.8 |
| 4,406,167 | 8/1983 | Maeda | 73/622 |
| 4,506,549 | 3/1985 | Thome | 73/582 |
| 4,523,470 | 6/1985 | Müller | 73/623 |
| 4,593,568 | 6/1986 | Telford | 73/623 |
| 4,663,727 | 5/1987 | Saporito et al. | 364/551 |
| 4,821,943 | 4/1989 | Gaudin et al. | 228/45 |

FOREIGN PATENT DOCUMENTS

| 0251698 | 1/1988 | European Pat. Off. |
| 0276819 | 8/1988 | European Pat. Off. |
| 2396295 | 1/1979 | France |
| 2562670 | 10/1985 | France |

Primary Examiner—Brooks H. Hunt
Assistant Examiner—Meena Chelliah
Attorney, Agent, or Firm—Pollock, VandeSande & Priddy

[57] ABSTRACT

The device comprises a flexible pipe (15) having one of its ends in a zone (20) situated outside the water box (6) and its other end joined to a tubular probe-guide (16) supported by a handling device (13, 14) inside the water box (6). A sheath (21) is slideably mounted inside the flexible pipe (15) and has mounted at one of its ends a stop and a bush for guiding the ultrasonic probe (18). A Bowden cable (22) is mounted rotatably about its axis inside the sheath (21), and is integral at one of its ends with a profiled rotational driving part and joined at its other end, outside the water box (6), to a motor (24). The support for the probe (18) has a threaded part engaged in a tapped part of the guide bush and can be driven in rotation by a profiled part integral with the end of the Bowden cable (22). The support for the probe (18) is thus driven in rotation and axial translation so as to perform a helical movement.

6 Claims, 7 Drawing Sheets

DEVICE FOR THE ULTRASONIC NON-DESTRUCTIVE TESTING OF A CIRCULAR WELD INSIDE A STEAM GENERATOR TUBE

FIELD OF THE INVENTION

The invention relates to a device for the ultrasonic non-destructive testing of a circular weld inside a steam generator tube of a pressurized-water nuclear reactor.

BACKGROUND OF THE INVENTION

The steam generators of pressurized-water nuclear reactors have a bundle of U-shaped tubes, the ends of which are crimped inside holes passing through a tube plate, and are flush with one of the sides of the tube plate forming its inlet side. A water box is delimited, in the bottom part of the steam generator, by the tube plate, the inlet side of which forms the top wall of the water box.

The pressurized water constituting the reactor coolant flows inside the tubes of the bundle, which tubes ensure thermal contact, in the part of the steam generator located above the tube plate, between the pressurized cooling water and the feed water in contact with the external surface of the tubes. The heat of the reactor cooling water thus ensures that the feed water is heated and vaporized.

The tubes of the bundle form a part of the barrier separating the primary cooling water of the reactor from the feed water. It is therefore necessary to check the walls of the tubes and ensure that they are undamaged, so as to prevent any leaks of the pressurized water in which radioactive elements are suspended, inside the secondary part of the steam generator containing the feed water.

The steam generators of pressurized-water nuclear reactors are intended to operate for very long periods during which their tubes may be subject to a certain degrading action, for example as a result of corrosion by the primary water or the feed water.

Cracks affecting the wall of the tubes may appear in certain zones and in particular in the vicinity of the outlet side of the tube plate. Such cracks result in frequently troublesome leaks of primary water into the feed water.

When such leaks are detected, the tubes of the steam generators affected by leaks are repaired during a down period reserved for maintenance of the reactor. These repairs may be performed by lining the cracked area of the tube. Such an operation consists in fixing a sleeve inside the tube, in the area which is cracked. The tube is expanded at each of its ends, on either side of the cracked area.

To ensure that there is a perfectly leak-proof joint between the sleeve and the tube, a circular weld is effected in the vicinity of each of the ends of the sleeve, so that there is a metallurgical type joint between the sleeve and the tube. This weld is preferably effected by means of the TIG method, i.e., a method using a tungsten electrode and an inert-gas atmosphere in the welding zone.

The quality and sealing action of the joint depend on the quality of the weld effected, so much so that it is preferable to check carefully the condition of the welds joining the sleeves and the tubes, before again starting up the steam generator.

The inside of the steam generator tubes and the walls of the water box are fairly heavily contaminated after a certain period of operation of the steam generator, such that the fitting and final welding of the sleeves require precautionary measures to prevent the personnel carrying out the repairs from being exposed to large doses of radioactivity.

Tools have been designed to perform the fitting and final welding of the sleeves inside contaminated steam generator tubes.

On the other hand, a testing device for checking the condition of the welds performed on the sleeves and preventing contamination of the personnel used to carry out these checks is not known.

Handling devices are known which can be positioned inside the water box of a steam generator and which allow a tool or a test probe to be introduced inside any tube of the bundle, via its end flush with the inlet side of the tube plate.

However, no device is known for positioning and using a non-destructive weld testing probe such as an ultrasonic probe, in order to scan a circular zone of limited length inside a tube.

SUMMARY OF THE INVENTION

The object of the invention is to provide a device for the ultrasonic non-destructive testing of a circular weld inside a steam generator tube of a pressurized-water nuclear reactor having a bundle of tubes, the ends of which are crimped inside holes passing through a tube plate having an inlet side with which the ends of the tubes are flush and forming a wall of a water box receiving the cooling water of the reactor, testing being performed using a detection means comprising at least one ultrasonic probe introduced inside the tube from the water box side, with the aid of a handling means arranged inside the water box and enabling the probe to be positioned inside any tube of the bundle, this device enabling the weld to be carefully tested, without exposing the personnel performing the test to the radiactivity existing inside the water box of the steam generator.

To this end, the device according to the invention comprises:

a flexible pipe having one of its ends in a zone situated outside the water box and its other end connected to a tubular probe-guide supported by the handling means;

a sheath mounted slideably inside the flexible pipe, having at one of its ends a stop and a bush for guiding the probe and with its other end, outside the water box, emerging from the end of the flexible pipe;

a Bowden cable mounted for rotation about its axis, inside the sheath, integral at one of its ends with a profiled rotational driving part and connected at its other end, outside the water box, to a means for driving the said Bowden cable in rotation about its axis;

a probe support comprising a threaded part engaged inside a tapped part of the guide bush and an aperture with a shape corresponding to the profiled cross-section of the rotational driving part, for driving the probe support in rotation and axial translation, by causing the Bowden cable to rotate, and means for supplying coupling liquid to the zone of the tube to be tested and for recovering the coupling liquid.

BRIEF DESCRIPTION OF THE DRAWINGS

So that the invention may be more clearly understood, a description will now be given, by way of example, with reference to the accompanying drawings, of an embodiment of a non-destructive testing device according to the invention and its use for testing circular welds inside steam generator tubes which have been lined with sleeves.

DESCRIPTION OF PREFERRED EMBODIMENT

Figure 1:
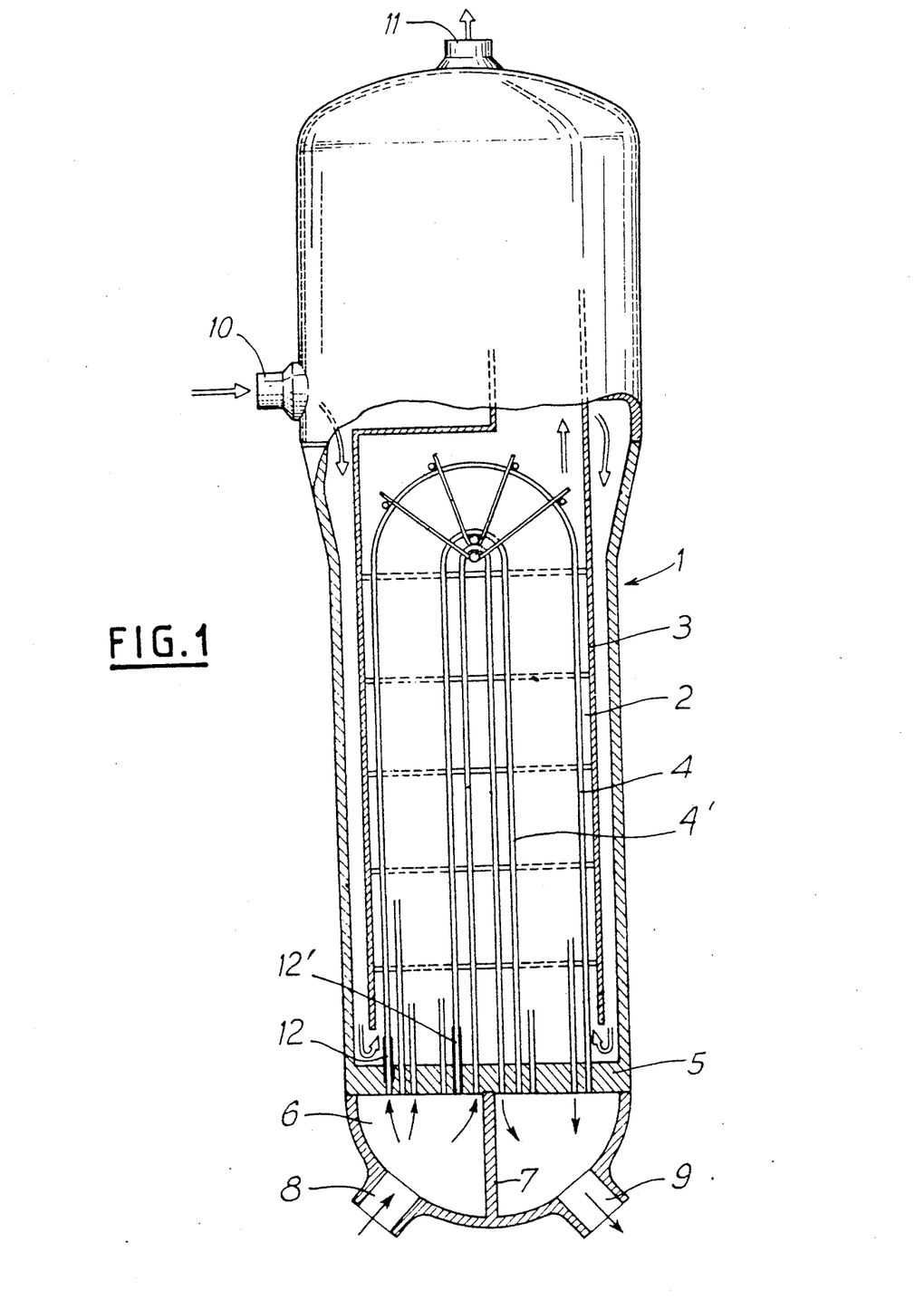
FIG. 1 is a partially sectioned elevation view of a steam generator of a pressurized-water nuclear reactor.

FIG. 1 shows a steam generator 1 of a pressurized-water nuclear reactor. The steam generator 1 has a bundle of tubes 2 located inside a bundle casing 3 in the central part of the steam generator 1. The ends of each of the tubes 4 of the bundle which is U-shaped at the top are fixed in a tube plate 5 separating the part of the steam generator enclosing the bundle 2 from a water box 6 consisting of two parts separated by a partition 7.

Each of the tubes of the bundle has one end fixed in a hole passing through the tube plate 5 on one side of the partition 7 and its opposite end fixed in a hole passing through the tube plate 5 on the other side of the partition 7. The pressurized cooling water of the nuclear reactor enters, via a duct 8, into one of the compartments of the water box 6 delimited by the partition 7 and then flows inside the tubes 4 of the bundle, emerging in the second compartment of the water box 6 having an outlet duct 9.

The feed water enters into the top part of the steam generator 1 via a duct 10, flows from the top downwards inside the peripheral space delimited by the bundle casing 3 inside the steam generator, and then from the bottom upwards in contact with the bundle 2 inside the casing 3, emerging in the form of steam in the top part of the steam generator, the feed water being heated and vaporized when it comes into contact with the tubes of the bundle inside which the pressurized cooling water of the reactor flows. The steam is discharged via the duct 11 located at the top end of the steam generator.

The tubes 4 of the bundle are subjected to a certain degree of wear and of corrosion during operation of the steam generator, such that these tubes are susceptibel to leaks at least in certain zones, after a certain period of operation of the steam generator.

The internal stressing of the tubes and the increased intensity of corrosion in the zone of the tubes situated in the vicinity of the upper side of the tube plate 5 result in a greater frequency of cracks and leaks in this zone.

In order to prolong the service life of the steam generator, the ends of the tubes affected by leaks must either be stopped up or the tubes must repaired by lining them with sleeves.

The sleeve-lining operation consists in introducing a sleeve into a tube which has a leak, so as to cover the leaking zone. The sleeve can be crimped by means of expansion inside the tube, this crimping operation being followed by welding the sleeve onto the tube in two circular zones on either side of the leaking zone. A perfectly leakproof joint between the sleeve and the tube is thus obtained, such that complete separation of the primary fluid and the feed water is again ensured for the tube in question.

FIG. 1 shows a sleeve 12 used to repair a steam generator tube in the vicinity of the upper side of the tube plate. As mentioned above, this zone is the zone where repairs to the tubes of a steam generator are most frequently carried out.

This sleeve 12 is positioned inside the tube so that its bottom end is located inside the tube plate 5 and its top end is located above the upper side of this tube plate 5.

In the case of the sleeve 12, the tube 4 is a peripheral tube of the bundle below which there is only a limited amount of clearance inside the hemispherically shaped water box 6. Therefore, a sleeve 12 of limited length is used, the bottom end of which is located at a cetain distance from the inlet side of the tube plate 5.

In the case of tubes 4 located towards the central part of the bundle, it is possible to use sleeves of greater length, such as 12', the bottom end of which is located close to the inlet side of the tube plate 5.

In all cases, the ends of the sleeves must be crimped inside the tube, and these sleeves welded onto the tube in two circular zones close to its ends.

These operations must be performed and controlled from outside of the water box, thereby requiring the use of special devices which have been designed by the applicant.

Such special tools are described, for example, in French Patents Nos. 86-06342 and 87-09872.

When the sleeve has been welded on either side of the leaking zone of the tube, this tube forming a barrier between the primary fluid and the feed water is, in principle, made perfectly leakproof again.

However, the difficulty in performing the welding operation may result in non-uniform quality of the welds, which may have incipient cracks, irregularities or even non-leakproof zones.

It is thus desirable to provide means for testing the circular welds performed inside the tube.

Figure 2:
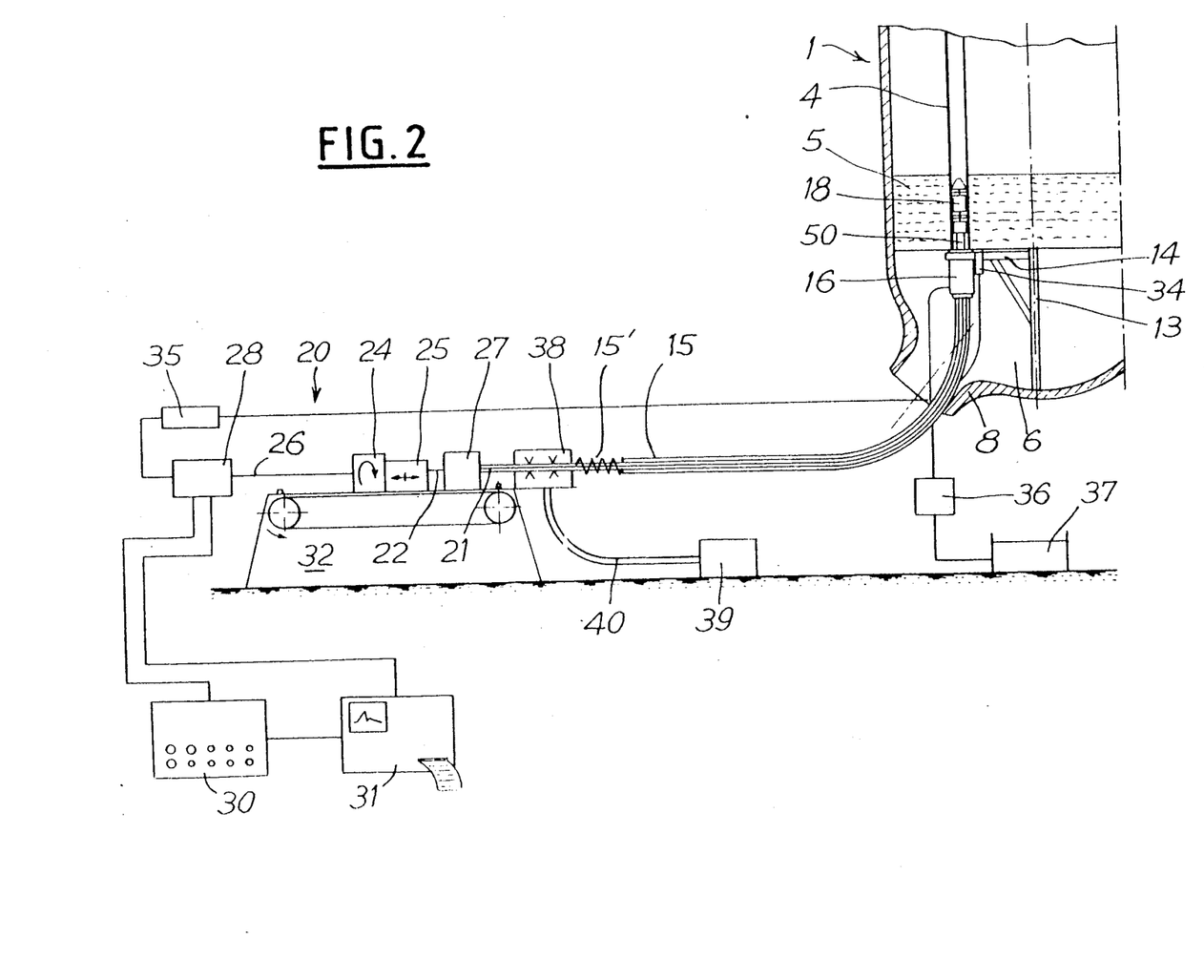
FIG. 2 is a schematic, sectioned elevation view of a device for the non-destructive testing of circular welds inside tubes of a steam generator.

FIG. 2 shows the assembly constituting the device according to the invention, which enables the circular zones welded inside a steam generator tube to be tested.

The device has been shown in its working position inside a tube 4 of a steam generator 1, inside which a sleeve has been fitted according to the method described above.

In order to perform testing of the welds effected inside any tube 4 of the bundle, use is made of a handling means 13 arranged inside the water box 6 and comprising an arm 14 the movements of which are remote-controlled and which is able to position a tool inside the axial extension of any tube of the bundle, below the tube plate 5.

Such a handling device is known from the prior art and may be fixed by one or more columns arranged according to the height of the water box or by fixing elements inside tubes passing through the tube plate 5.

The device according to the invention comprises a flexible pipe 15, one end of which is integral with a tubular element 16 connected to the end of the arm 14 of the handling means 13 and which forms a guiding element for a test probe 18 which is to be introduced inside the tube 4.

The opposite end of the flexible pipe 15 consisting of a spring device 15' is located outside the water box, in the region of a testing and control station 20.

A sheath 21 is mounted inside the pipe 15 along its entire length and has an end part located outside the pipe 15, in the region of the testing and control station 20.

The device comprises, moreover, a Bowden cable 22 which is mounted inside the sheath 21 and the end of which is connected to a motor 24 enabling the said Bowden cable to be rotated about its axis, inside the sheath 21. An angle encoder 25 arranged on the output side of the motor 24 allows the rotations performed by the Bowden cable 22 to be controlled and recorded.

The Bowden cable 22, which is tubular in shape, has passing through it, along its entire length, a coaxial cable 26 which is connected, at one of its ends, to the probe 18 and, at its other end, to modules 30 and 31 for processing data supplied by the probe, via a rotating collector 27 and an electrical connection element 28.

The motor 24, the encoder 25 and the rotating collector 27 are arranged on the mobile part of a device 32 for axially displacing the movable assembly inside the flexible pipe 15.

The handling means 13 comprises a device 34 for raising and lowering the tubular guide 16 so as to bring it into contact with or move it away from the end of a tube on the lower side of the tube plate 5. The device 34 is controlled by a solenoid valve 35 located, outside the water box, in the testing and control station. The test probe 18 is an ultrasonic probe requiring the presence of a coupling liquid inside the tube when used to test welds.

Coupling water can be conveyed by a pump 36 supplied by a capacitor 37, inside the tube 4, via the tubular element 16, when the latter is brought into contact with the end of the tube 4 by the vertical displacement device 34.

When the test inside the tube 4 has been completed, the coupling water is recovered by means of a recovery device 38 fixed on the flexible pipe 15, communicating with the internal volume of this pipe and connected to a suction device 39, via a pipe 40.

Figures 3, 3A:
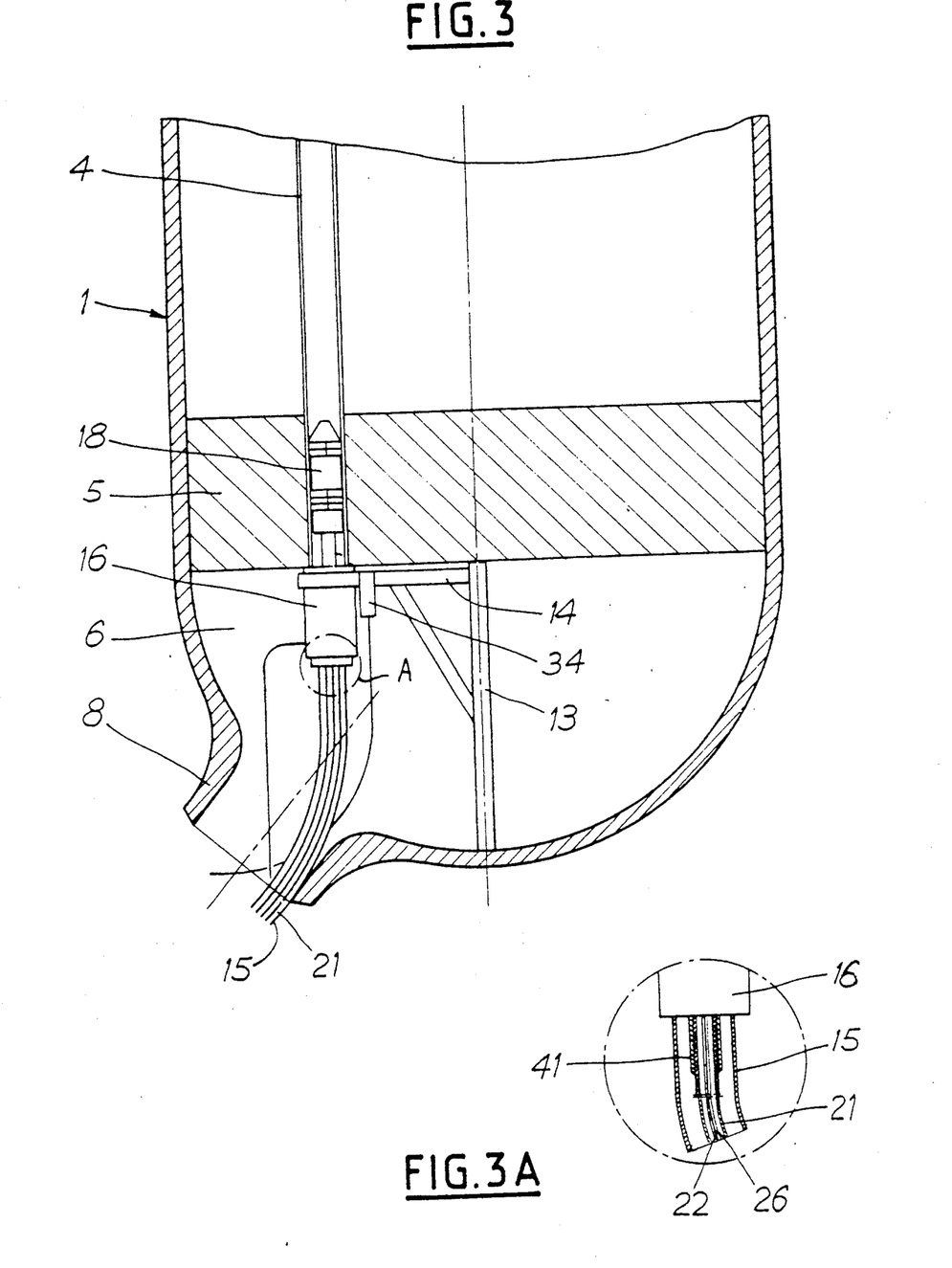
FIG. 3 is a view, on a larger scale, of the part of the device shown in FIG. 2 located inside the steam generator.
FIG. 3A is a view, on a larger scale, of the detail A of FIG. 3.

In FIGS. 3 and 3A, it can be seen that the end of the sheath 21 is integral with an annular-shaped stop 41 engaged partially inside the tubular element 16, when the device is in the working position, as shown in FIGS. 2, 3 and 3A.

Figure 4A:
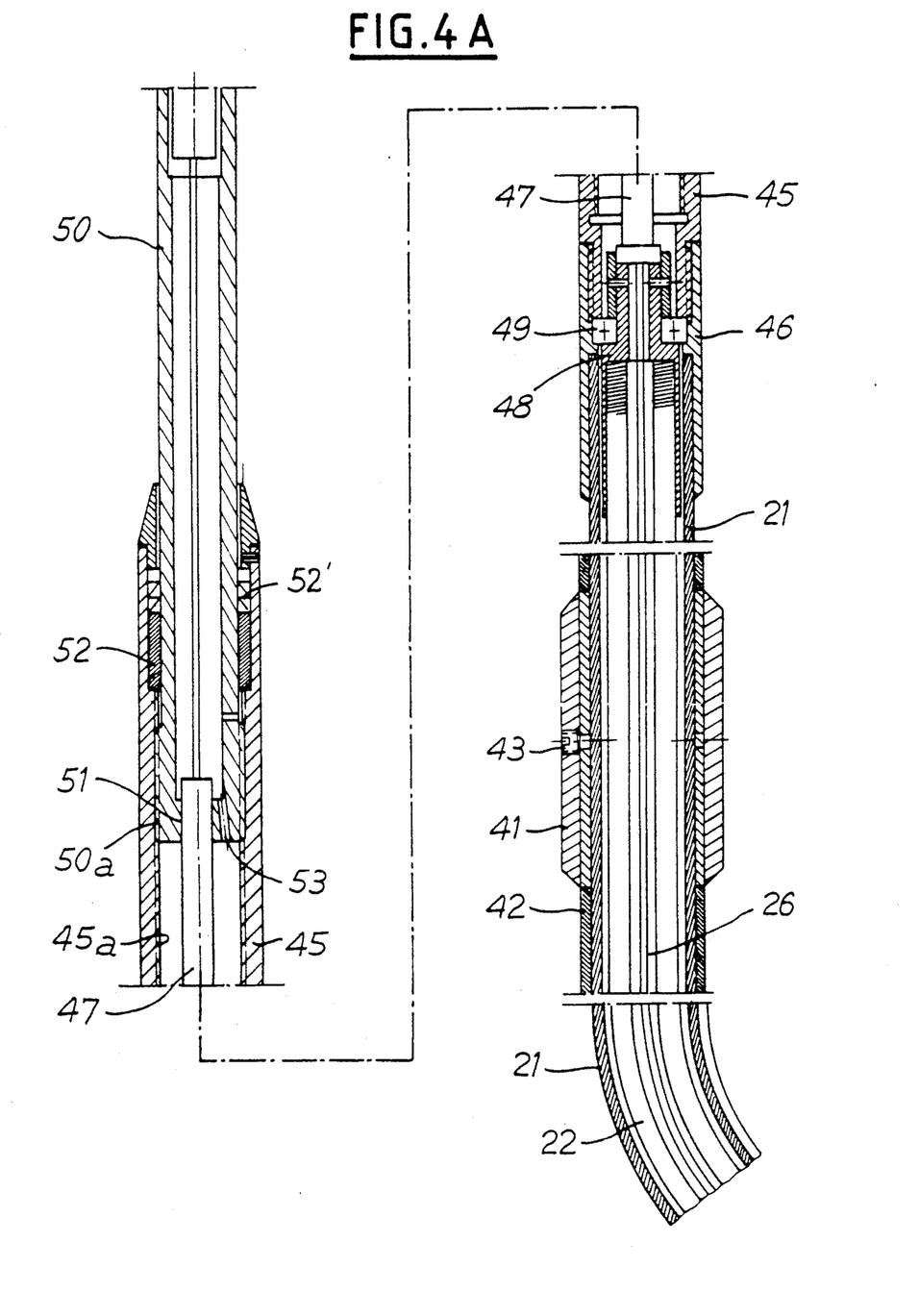
FIGS. 4A and 4B are longitudinal sections through the bottom part and top part, respectively, of an ultrasonic test probe and its support.
Figure 4B:
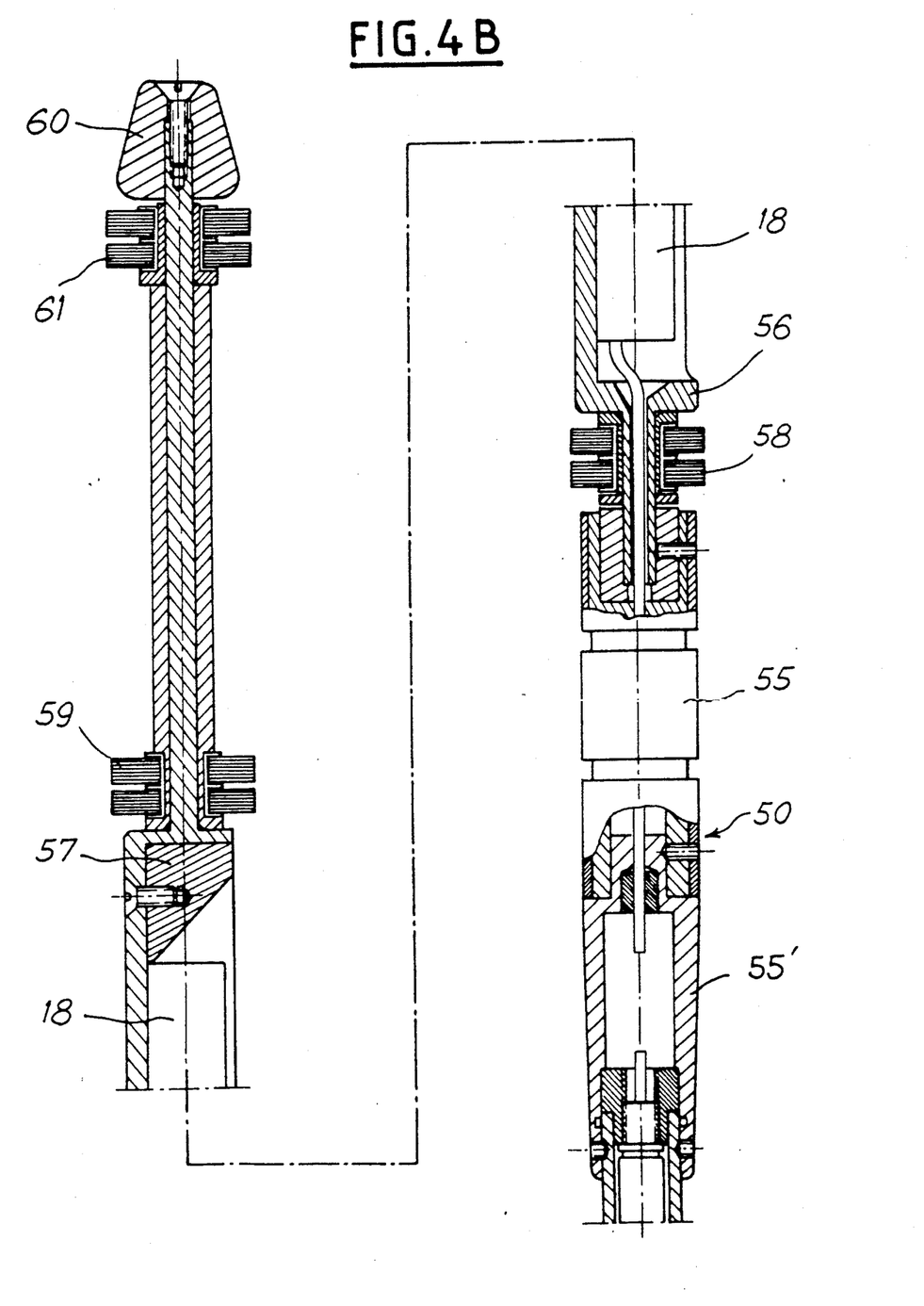

FIG. 4A shows the bottom part of the coaxially arranged assembly carrying the probe 18 shown in FIG. 4B.

This assembly with a coaxial structure comprises, as mentioned above, the sheath 21, the Bowden cable 22 and the coaxial cable 26. This assembly passes inside the flexible pipe 15 so as to ensure that the control and testing station 20 is joined to the waterbox 6 of the steam generator.

The flexible sheath 21 consists of a plastic tube which can be strengthened so as to increase its mechanical properties.

The Bowden cable 22 consists of a flexible metal tubular structure capable of transmitting a rotational movement along its entire length, while possessing a very large degree of flexibility.

The coaxial cable 26 is a simple cable for transmitting small-diameter measurements, positioned along the axis of the coaxial assembly.

The stop 41 consists of an annular piece integral with a sheath 42 slideably mounted on the sheath 21 so as to be able to adjust the position of the stop 41. The position of this stop can be fixed by means of a screw 43 passing through the stop 41.

As can be seen in FIGS. 3 and 3A, the stop 41 bears, inside the tubular part 16 held at the inlet of the tube 4 by the arm 14, against a corresponding stop surface determining the position of the probe 18 inside the tube 4.

Thus, according to the position of the stop 41, it is possible to position the probe 18 inside the tube so as to test the lower weld or the upper weld of a sleeve fixed inside the tube 4, whether this sleeve is a short sleeve such as the sleeve 12 shown in FIG. 1 or a sleeve of normal length such as the sleeve 12'.

A bus 45 is fixed to the end of the sheath 21, above the stop 41, by means of a connection piece 46 which is rigidly fixed to the end of the sheath 21 and onto which the bush 45 is fixed by means of screwing.

The bush 45 is tapped along a section 45a of its internal bore. A threaded end part of the probe support 50 is engaged by means of screwing inside the part 45a of the bush 45.

The end of the Bowden cable 22 is integral with a profiled part 47 having a square cross-section and arranged along the axis of the bush 45. The tubular-shaped probe carrier 50 has at its threaded bottom end a base with an aperture 51 having a square cross-section, into which aperture the part 47 is slideably engaged.

Thus, when the Bowden cable 22 is rotated about its axis by the motor 24 arranged outside the water box, the profiled part 47 drives the probe support 50 both in rotation about the axis of the bush 45 and in translation along this axis, the threaded part 50a of the probe support 50 forming a nut movably mounted inside the tapped part 45a of the bush 45.

Two lip seals 52' are arranged inside the top part of the bush 45. Guiding is ensured by means of a ring 52.

The base of the probe support also has formed in it a channel 53 arranged laterally relative to the aperture 51.

With reference to FIG. 4B, it can be seen that the bottom part of the probe carrier 50 is connected by means of a Cardan joint 55 to the top part of the probe carrier so as to facilitate positioning and orientation of this top part of the probe carrier inside the tube 4 in which the test is being performed.

The top part of the probe carrier comprises a support 56 onto which the actual probe 18 is fixed and a mirror 57, the surface of which, inclined, depending on the type of weld, at a variable angle relative to the axis of the bush 45 and the probe carrier 50, is used to reflect the outgoing and incoming ultrasonic signals emitted or received by the probe 18 consisting of an ultrasonic transducer.

On either side of the support 56, the probe carrier has annular brushes 58 and 59 which serve to guide and center the support 56 and the probe 18 inside the tube or the sleeve inside which the probe carrier is engaged.

The end part of the probe support 50 consists of a profiled guiding head 60, underneath which there is located an annular-shaped brush 61 for centering and guiding the top part of the probe carrier inside the tube 4.

Figure 5:
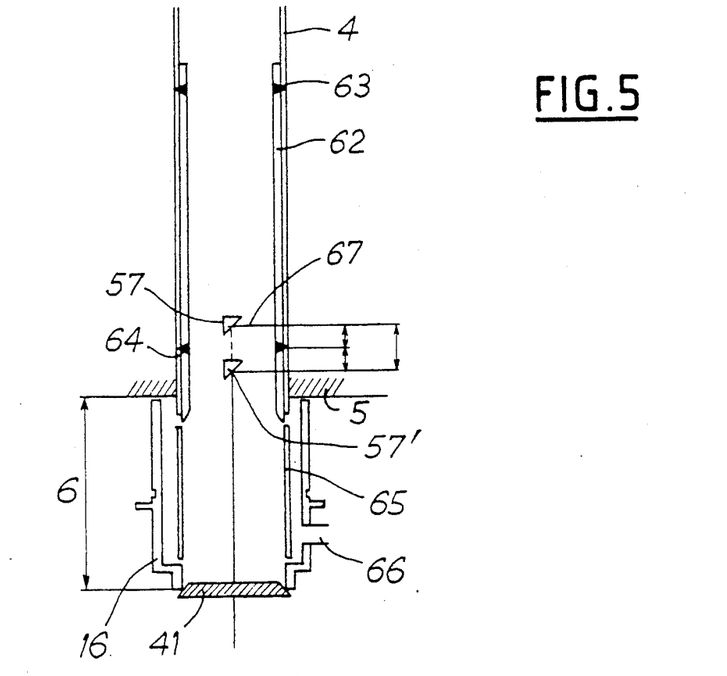
FIG. 5 is a section through a part of the tube plate of a steam generator, underneath which a probe guide for a testing device according to the invention is positioned.

FIG. 5 shows schematically a repair sleeve 62 fixed inside a tube 4 of the steam generator. Fixing of the sleeve 62 is completed by upper and lower circular welded joints 63 and 64, respectively, which enable a leakproof joint between the sleeve 62 and the tube 4 to be obtained.

Certain elements of the test device described above have been shown, schematically, in the position which they assume during testing of the lower weld 64.

The tubular probe guide 16 is kept pressed against the lower side of the tube plate 5 by the handling means arranged inside the water box 6.

A calibration collar 65 is arranged inside the probe guide 16 in a coaxial position relative to the probe guide, the tube 4 and the sleeve 62.

A lateral water inlet nozzle 66 enables the connection between the probe guide 16 and the pump outlet pipe 36 to be effected.

The stop 41 fixed on the sheath 21 of the coaxial assembly movable inside the pipe 15 bears against a stop surface located at the inlet of the tubular probe guide 16.

The position of the stop 41 at the end of the sheath 21 determines the position of the probe 18 and of the mirror 57 ensuring the emission and capture of an ultrasonic beam 67 in the radial direction towards and away from the wall of the sleeve 62.

The mirror 57 has been shown in two end positions 57, 57' during scanning of the sleeve zone corresponding to the welded zone 64.

Figure 6:
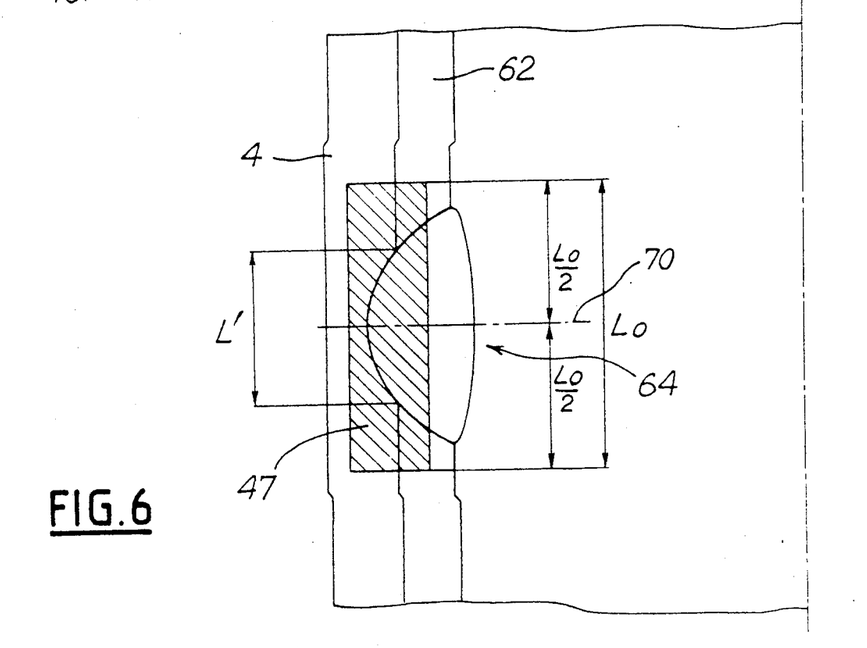
FIG. 6 is a view, on a larger scale, of a weld joining together a sleeve and a tube of the steam generator.

This welded zone 64 is shown on a larger scale in FIG. 6. Testing of the weld consists in performing a longitudinal scan of the welded zone over a distance L, symmetrically relative to the center plane 70 of the annular weld 64.

In the case of the steam-generator tubes, scanning will be performed over a distance L substantially equal to 24 mm, allowing a minimum scan of 5 mm on either side of the center plane 70 of the weld.

The ultrasonic beam conveyed radially by the mirror 57 is reflected in particular by the interface between the sleeve 62 and the tube 4, so as to return to the mirror 57 and the transducer 18. The signal reflected by the sleeve/tube interface is recorded using a gate synchronized with the surface echo, and then comparatively processed at a given threshold. The continuity of the weld is thus verified.

Moreover, the length L' of the resistant zone of the weld corresponding to the intersection of the welded zone 64 with the sleeve/tube interface is measured, during scanning by the ultrasonic signals. This zone with a length L' corresponding to the zone of the sleeve 62 joined metallurgically to the tube 4 ensures that the joint is leakproof.

In the case of steam tubes and sleeves used in the generators, the length of the welded zone LO taken into account is substantially equal to 10 mm, this zone extending for 5 mm on either side of the center plane 70.

It will be checked that the zone L' has a length at least equal to 2 mm.

Figures 7, 8:
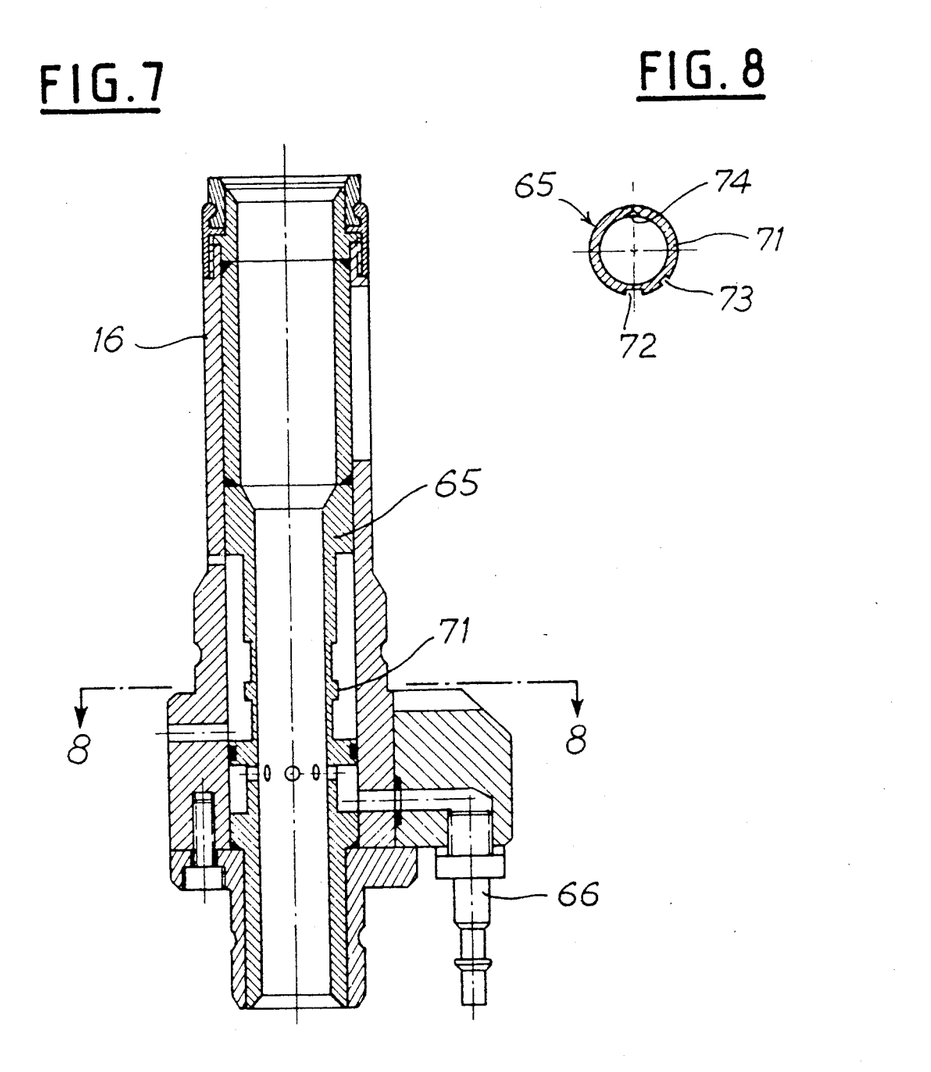
FIG. 7 is a section through a probe guide of the device according to the invention and a calibration tube of the probe.
FIG. 8 is a section, along line 8—8, of the calibration tube shown in FIG. 7.

FIGS. 7 and 8 show, in greater detail, the tubular probe guide 16, the bottom end of which has a frusto-conical bearing surface for the stop 41 of the movable testing device assembly.

This frusto-conical surface is machined at the end of a calibration tube 65 fixed inside the tubular probe guide 16.

The calibration tube 65 has an annular test part 71, the cross-section of which is visible in FIG. 8. In this annular part, the calibration tube has notches 72 and 73 with different widths in the circumferential direction, as well as an internal conical opening 74 at an angle of 90° on a part of the wall of the calibration tube 65.

The notches 72 and 73 and the cone 74 represent defects of the welded zone, for which the ultrasonic signals are recorded before the actual weld testing operations. These signals are recorded for a predetermined position of the device 32. During this phase, the annular brushes 58 ensure that there are no leaks.

Calibration, like the actual test, is performed using water as the coupling liquid, this water being introduced inside the tubular probe guide 16 in contact with the lower side of the tube plate, via the nozzle 66.

There now follows a description, with reference to all the drawings, of an operation for testing a leakproof weld of a sleeve inside a tube 4 of the steam generator.

The handling means 13, the arm 14 of which has the tubular probe guide 16 at its end, is positioned inside the water box 6 of the steam generator. The arm 14 enables the probe guide tube 16 to be positioned vertically inside a tube 4, so that the end of the probe guide bears against the lower side of the tube plate.

The stop 41 is adjusted so that the probe 18 and its mirror 57 are positioned in a zone allowing one of the welds of the sleeve 62, for example the lower weld 64, to be tested, as explained above.

The movable coaxial testing assembly is introduced inside the flexible pipe 15 via its end outside the water box 6. The probe is positioned, initially, opposite the test part of the calibration tube, inside the probe guide 16.

Coupling water is introduced into the probe guide by the pump 36 and via the nozzle 46.

The movable coaxial assembly is positioned inside the pipe 15 by the displacement device 32 exerting a thrusting force on the end of the sheath 21.

Rotation of the probe is effected by the motor 24, by means of the Bowden cable 22 mounted inside the sheath 21.

The signal corresponding to the notches 72 and 73 and to the conical hole 74 of the calibration tube 65 is recorded as the reference element.

The movable coaxial assembly is then displaced until the stop 41 bears against the end part of the calibration tube 65. The displacements are effected, as before, by the device 32. The spring device 15' enables the stop 41 to be positioned on the probe guide 16 and thus ensures that there is no leakage of the coupling liquid.

The stop 41 is adjusted so that the probe 18 and its mirror 57 are now in the welded zone 64.

The motor 24 is operated and causes rotation of the Bowden cable 22 in a direction such that the probe carrier 50 is raised inside the threaded bush 45 up to its highest point. The motor then stops, the probe and its mirror being in the highest position corresponding to the top end of the zone to be tested, in the vicinity of the weld 64.

At the same time, the coupling water is introduced inside the probe guide 16 and hence inside the tube 4. When the level reaches the mirror 57, an echo is reflected by the surface of the sleeve 62. A signal then causes the pump 36 to stop. The water is used as the coupling liquid during the ultrasonic test.

The motor 24 is then made to rotate in the direction opposite to the direction above so as to effect, at a controlled speed, helical displacement of the probe carrier and the probe 18 inside the sleeve, over a distance L equal to 24 mm.

The ultrasonic probe rotates at 2.7 revolutions per second and performs a helical movement with a pitch of 0.4 mm.

The signals are captured by the coaxial cable 26 and processed by the units 30 and 31.

When testing inside a tube 4 has been completed, the coupling water is recovered by means of the flexible pipe 15, the device 38, the pipe 40 and the suction device 39.

The movable coaxial assembly and the probe 18 are pulled inside the flexible pipe 15 by means of the displacement device 32, and the arm 14 of the handling device 13 is positioned opposite the next tube to be tested.

The operations can be continued as described above.

Using the device according to the invention, it is thus possible to perform very precise testing of the leakproof welds of a sleeve inside a steam-generator tube, by displacing the probe in a helical movement so as to scan the entire welded zone at a precisely defined height.

It should be noted that testing is always performed during displacement of the probe in the same direction, i.e., from the top downwards.

Positioning of the probe inside the tube is, moreover, very easy to achieve owing to the flexible guiding pipe 15 and the stop 41 cooperating with the tubular probe guide 16.

Furthermore, the longitudinal and rotational displacements of the probe are obtained without difficulty in a very precise manner, using a single bidirectional motor arranged outside the water box.

It is possible to use means for displacing the probe and movable coaxial assembly other than those described and other means for introducing and recovering the coupling liquid inside the tube to be tested.

The probe according to the exemplary embodiment described may be replaced by a detection assembly comprising several ultrasonic probes each connected to a coaxial cable.

The means for processing the probe signal may be of any type and may comprise any type of display or recording means inside the testing station 20.

Finally, the device according to the invention is suitable for the non-destructive testing of any circular weld inside a tube of a steam generator of a pressurized-water nuclear reactor and for any other type of testing over a given zone; in such case, only the probe head shown in FIG. 4B must be changed in the region of the connector 55', and the processing method adapted.

I claim:

1. Device for ultrasonic non-destructive testing of a circular weld (63, 64) inside a steam generator tube (4) of a pressurized-water nuclear reactor having a bundle of tubes (2) ends of which tubes are crimped inside holes passing through a tube plate (5) having an inlet side with which said ends of said tubes (4) are flush and forming a wall of a water box (6) receiving cooling water of said reactor, testing being performed using a detection means comprising at least one ultrasonic probe (18) introduced inside a said tube from said water box side with the aid of a handling means (13, 14) arranged inside said water box and enabling said probe to be positioned inside any tube or the bundle, said device comprising (a) a flexible pipe (15) having one end thereof in a zone (20) located outside the water box (6) and its other end connected to a tubular probe guide (16) supported by said handling means (13, 14);

(b) a sheath (21) slideably mounted inside said flexible pipe (15), said sheath having at one end thereof a stop (41) and a bush (45) for guiding said probe and its other end, outside said water box (6), emerging from said one end of said flexible pipe (15);

(c) a flexible metal tubular structure (22) transmitting a rotational movement mounted for rotation about its axis inside said sheath (21), said structure being integral at one of its ends with a profiled rotational driving part (47) and connected at its other end, outside said water box (6), to means (24) for driving said flexible metal tubular structure in rotation about its axis;

(d) a probe support (50) comprising a threaded part (50a) engaged inside a tapped part (45a) of said bush (45) an aperture (51) having a shape corresponding to a profiled cross-section of said rotational driving part (47), for driving said probe support (50) in rotation and axial translation, by causing said flexible metal tubular structure (22) to rotate; and (e) means (36, 37, 38, 39, 40) for supplying coupling liquid to a zone of said cube to be tested and for recovering said coupling liquid.

2. Testing device according to claim 1, wherein said stop (41) has a position which is adjustable along the axial direction of said sheath (21).

3. Testing device according to claim 1, wherein said tubular probe guide (16) has a bearing surface for said stop (41) fixed on said sheath (21).

4. Testing device according to claim 1, wherein said tubular probe guide (16) encloses a tube (65) for calibrating said probe (18).

5. Device according to claim 1, wherein said probe support (50) comprises at least two parts arranged in sequence in the axial direction and joined by a universal joint (55).

6. Device according to claim 1, wherein said coaxial assembly consisting of said sheath (21) having, mounted on an end of said sheath said probe (18), said flexible metal tubular structure (22) and at least one coaxial cable (26) for transmitting the signals of said detection means, arranged in the central part of said flexible tubular metal structure (22), is connected, at its end located outside said water box (6), to a device (32) for effecting axial sliding displacement inside said pipe (15) itself integral with a spring device (15').

* * * * *